United States Patent [19]

Gaffar et al.

[11] Patent Number: 4,537,765

[45] Date of Patent: Aug. 27, 1985

[54] PEROXYDIPHOSPHATE TOOTHPASTE COMPOSITION

[75] Inventors: Abdul Gaffar, Somerset; Calvin B. Davis, North Brunswick; John J. Donohue, Neshanic; Debbie Moy, Livingston, all of N.J.

[73] Assignee: Colgate-Palmolive Company, New York, N.Y.

[21] Appl. No.: 506,183

[22] Filed: Jun. 21, 1983

Related U.S. Application Data

[63] Continuation of Ser. No. 361,180, Mar. 24, 1982, abandoned.

[51] Int. Cl.³ .......................... A61K 7/16; A61K 7/20
[52] U.S. Cl. ........................ 424/53; 424/49; 424/57
[58] Field of Search .............. 424/52, 53, 57

[56] References Cited

U.S. PATENT DOCUMENTS

| | | | |
|---|---|---|---|
| 4,041,149 | 8/1977 | Gaffar et al. | 424/52 |
| 4,177,258 | 12/1979 | Gaffar et al. | 424/52 |
| 4,183,915 | 1/1980 | Gaffar et al. | 424/52 |
| 4,273,759 | 6/1981 | Gaffar et al. | 424/52 |
| 4,309,410 | 1/1982 | Gaffar | 424/52 |
| 4,431,631 | 2/1984 | Clipper et al. | 424/52 |

*Primary Examiner*—Shep K. Rose
*Attorney, Agent, or Firm*—Herbert S. Sylvester; Murray M. Grill; Robert L. Stone

[57] ABSTRACT

A toothpaste composition containing a peroxydiphosphate salt and optionally a fluorine-providing anticaries agent as substantially the sole oral chemically active agents, in combination with specially selected polishing material, thickeners, and humectants.

20 Claims, No Drawings

PEROXYDIPHOSPHATE TOOTHPASTE COMPOSITION

This is a continuation of application Ser. No. 361,180, filed Mar. 24, 1982, now abandoned.

This invention relates to stabilized toothpaste compositions and especially to such compositions containing a peroxydiphosphate salt (PDP) preferably the tetrapotassium salt (KPDP), and optionally fluorine-providing anticaries agent as substantially the sole oral chemically active agents.

It is known in the art that hydrogen peroxide and other peroxygen-containing agents are effective against caries, dental plaque, gingivitis, periodontitis, mouth odor and tooth stains. In fact, the essential active PDP employed herein has been previously disclosed as an effective anti-odor agent in an oral composition. Thus, U.S. Pat. No. 4,041,149 issued Aug. 9, 1977 to Maria Gaffar, Abdul Gaffar (applicant herein) and John Hauschild discloses the effectiveness of such oral compositions, the PDP being activated by the salivary phosphatases to generate hydrogen peroxide and/or active or nascent oxygen which deodorizes the oral cavity.

Other oral compositions have been prepared in which a PDP salt is employed as an additive to inhibit the stains normally produced by the essential oral chemically active agent in the compositions. More particularly, U.S. Pat. No. 4,273,759 issued June 16, 1981 to Abdul Gaffar and Maria C. Gaffar discloses oral compositions containing PDP salts to inhibit stains normally produced by cationic nitrogen-containing antibacterial antiplaque agents and U.S. application Ser. No. 117,410 filed Jan. 31, 1980 by Abdul Gaffar, now U.S. Pat. No. 4,309,410, discloses oral compositions containing PDP salts to inhibit stains normally produced by a tranexamic acid antigingivitis agent.

It is also known however that most peroxy compounds such as hydrogen peroxide and metal peroxides such as magnesium peroxide are unstable in storage, continuously losing the ability to release active or nascent oxygen over relatively short periods of time, especially in the presence of various other incompatible inorganic and organic materials such as many of the usual excipients in oral compositions, especially toothpaste (including dental cream) compositions. Thus, in French Pat. No. 2325304 (75 29482) published Apr. 22, 1977, this problem is recognized and solved by a relatively difficult and costly means involving preventing the peroxidized component such as magnesium peroxide from contacting an acidic material reactive therewith, as by coating said component and acidic material with suitable excipients, prior to and until the moment of use in the oral cavity.

PDP salts are regarded as substantially more stable than hydrogen peroxide and magnesium peroxide. In said U.S. Pat. No. 4,041,149 it is disclosed that a 10% aqueous solution of the preferred KPDP shows no active oxygen loss after 4 months at 25° C. and a loss of 3% after 6 months at 50° C. It was accordingly concluded, and so indicated in the patent, that "this stability permits long shelf-life of oral compositions containing said peroxydiphosphate compound".

The aforesaid conclusion has however been found to be for the most part unjustified. Extensive experiments with oral compositions containing KPDP in combination with a variety of common excipients such as polishing material (dental abrasives), humectants, thickeners, flavors and the like have established hitherto unknown incompatibilities resulting in unduly short storage stability or shelf-life, premature loss of active oxygen, impairment of the desired functions of the several components of the compositions and/or unacceptable chemical and/or physical and/or cosmetic properties of the compositions and the like.

It is an object of this invention to provide oral compositions which will not be subject to one or more of the above disadvantages and deficiencies. Another object of this invention is the provision of stable oral compositions containing a PDP salt, and optionally a fluorine-providing anticaries compound, as substantially the only oral chemically active agents. Still another object of this invention is the provision of methods for promoting oral hygiene employing such compositions. Other objects and advantages will appear as the description proceeds.

In accordance with certain of its aspects, this invention includes the provision of a toothpaste composition comprising:
I an oral vehicle,
II as substantially the only oral chemically active agents,
  A. 0 to about 2 wt.% of a fluorine-providing anticaries compound and
  B. about 1 to about 7 wt.% of a peroxydiphosphate salt
III about 10 to about 75 wt.% of at least one polishing material selected from the group consisting of silica and hydrated alumina,
IV about 0.5 to about 10 wt.% of at least one thickener selected from the group consisting of colloidal silica, synthetic hectorite, poly(methyl vinyl ether/maleic anhydride), carboxyvinyl polymer, carboxymethyl cellulose, hydroxypropyl methyl cellulose, hydroxybutyl methyl cellulose, and hydroxyethyl cellulose, and
V about 5 to about 75 wt.% of polyethylene glycol as humectant.

The above defined oral chemically active IIA and B components are typically and preferably inorganic. These compositions which comprise mutually compatible components enable the attainment of one or more unexpected improvements such as unexpectedly improved storage stability or shelf-life, acceptable chemical and/or physical and/or cosmetic properties, retention of the desired functions of the individual components, and the like. As employed herein, the term "oral chemically active agent" refers to anticaries, antiplaque, antigingivitis, antiperiodontitis, antiodor and bleaching agents and the like which act chemically on, with respect to or in relation to the teeth, oral tissues and/or oral environment, in contrast to polishing material (dental abrasives) which act physically on the teeth and inert components which determine the properties of the oral composition per se such as thickeners, humectants, flavors, surfactants, sweeteners, colors, whiteners, brighteners, preservatives, and other conventional excipients. The essential PDP salts employed herein, especially KPDP, fall in the category of each of the aforementioned oral chemically active agents. The oral compositions of this invention, for similar reasons, are mutually exclusive of the antibacterial antiplaque compositions of the above mentioned U.S. Pat. No. 4,273,759 and the antigingivitis compositions of the above mentioned U.S. application Ser. No. 117,410.

Any of the alkali metal, alkaline earth metal, metal or ammonium peroxydiphosphates or their corresponding acid salts that are water-soluble to the extent of about 0.001 weight percent can be used in the compositions of this invention. Examples of these are tetrapotassium peroxydiphosphate ($K_4P_2O_8$), tetralithium peroxydiphosphate ($Li_4P_2O_8$), tetrasodium peroxydiphosphate ($Na_4P_2O_8$), tripotassium monosodium peroxydiphosphate ($K_3NaP_2O_8$), dipotassium disodium peroxydiphosphate ($K_2Na_2P_2O_8 2H_2O$), monopotassium trisodium peroxydiphosphate ($KNa_3P_2O_8$), monopotassium monosodium dihydrogen peroxydiphosphate ($KNaH_2P_2O_8$), trilithium monopotassium peroxydiphosphate ($Li_3KP_2O_8$), dilithium dipotassium peroxydiphosphate ($Li_2K_2P_2O_8$), monolithium tripotassium peroxydiphosphate ($LiK_3P_2O_8$), trilithium monosodium peroxydiphosphate ($Li_3NaP_2O_8$) dilithium disodium peroxydiphosphate ($Li_2Na_2P_2O_8$), monolithium trisodium peroxydiphosphate ($LiNa_3P_2O_8$), monolithium monosodium dihydrogen peroxydiphosphate ($LiNaH_2P_2O_8$), and monolithium monopotassium dihydrogen peroxydiphosphate ($LiKH_2P_2O_8$), in addition to dizinc peroxydiphosphate ($Zn_2P_2O_8$), tetraammonium peroxydiphosphate dihydrate( $(NH_4)_4P_2O_8 2H_2O$), and the acid salts of group 2 metals such as barium dihydrogen peroxydiphosphate ($BaH_2P_2O_8$), calcium dihydrogen peroxydiphosphate ($CaH_2P_2O_8$), and the like.

The preferred tetrapotassium peroxydiphosphate (KPDP) is a stable, odorless, finely divided, free-flowing, white, non-hygroscopic crystalline solid having a molecular weight of 346.35 and an active oxygen content of 4.5%. The potassium peroxydiphosphate is 47–51% water-soluble at 0°–61° C., but insoluble in common solvents such as acetonitrile, alcohols, ethers, ketones, dimethyl formamide, dimethyl sulfoxide, and the like. A 2% aqueous solution has a pH of about 9.6 and a saturated solution thereof a pH of about 10.9.

The essential PDP salt (or mixture thereof) is employed in an amount effective for achieving the desired therapeutic, antiodor, bleaching or other function, typically constituting about 1 to about 7 wt. %, preferably about 2 to about 5 wt. %, more preferably about 3 wt. %, of the instant oral compositions.

The fluorine-providing anticaries compounds optionally present in these oral preparations may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, calcium fluoride, a copper fluoride such as cuprous fluoride, zinc fluoride, a tin fluoride such as stannic fluoride or stannous chlorofluoride, barium fluoride, sodium fluorosilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of the fluorine-providing compound is dependent to some extent upon the type of compound, its solubility, and the type of oral preparation, but it must be a nontoxic amount. An amount of such compound which releases a maximum of about 1% of fluoride ion by weight of the preparation is considered satisfactory. Any suitable minimum amount of such compound may be used, but it is preferable to employ sufficient compound to release about 0.005 to 1%, and preferably about 0.1% of fluoride ion. Typically, especially in the cases of MFP, alkali metal fluorides and stannous fluoride, this component is present in an amount of about 0.01 to about 2% by weight, based on the weight of the preparation, and preferably in the range of about 0.05 to about 1 wt. %, especially about 0.76 wt. %.

To achieve the desired results herein, the component III polishing material should be selected from among silica, preferably hydrated alumina (alpha alumina trihydrate), both of which are per se conventional dental abrasive polishing material with average particle sizes ranging from about 0.1 to about 30 microns, preferably about 1.0 to about 15 microns. The following are illustrative of some preferred polishing material.

The silica polishing material may be in the form of crystalline silica having particle sizes up to 5 microns, a mean particle size of up to about 1.1 microns and a surface area of up to 50,000 cm.$^2$/gm., silica gels, Zeodent (e.g. Zeodent 49, 119) precipitated silica products of J. M. Huber Corporation, complex amorphous alkali metal aluminosilicates, and the like. The types of silica dental abrasives disclosed in U.S. Pat. No. 3,862,307 issued Jan. 21, 1975 may be employed.

When visually clear gels are employed, a polishing agent of silica xerogel or colloidal silica such as those sold under the trademark SYLOID (W. R. Grace and Co. e.g. Syloid 63, 64, 72 or 74) or under the trademark SANTOCEL as Santocel 100 and alkali metal aluminosilicate complexes are particularly useful, since they have refractive indices close to the refractive indices of gelling agent-liquid (including water and/or humectant) systems commonly used in dentrifrices.

Hydrated alumina, particularly the hydrated alumina sold by Alcoa as C333, which has an alumina content of 64.9% by weight, a silica content of 0.008%, a ferric oxide content of 0.003%, and a moisture content of 0.37%, at 110° C., and which has a specific gravity of 2.42 and a particle size such that 100% of the particles are less than 50 microns and 84% of the particles are less than 20 microns, is particularly desirable. Hydrated alumina has been found to be the most compatible polishing material herein.

The polishing material is generally present in amounts ranging from about 10 to about 75 wt.%, preferably about 35 to 65 wt.%, more preferably about 45 to about 55 wt. in these toothpaste compositions.

The thickener component IV, employed in proportions of about 0.5 to about 10 preferably about 1 to about 5, wt.% of the composition should be one or a mixture of the above-named members of the group. A preferred thickener is synthetic hectorite, a synthetic colloidal magnesium alkali metal silicate complex clay available for example as Laponite (e.g. XLG, XLS, D) marketed by Laporte Industries Limited. Laponite D analysis shows, approximately by weight, 58.00% $SiO_2$, 25.40% MgO, 3.05% $Na_2O$, 0.98% $Li_2O$, and some water and trace metals. Its true specific gravity is 2.53 and it has an apparent bulk density (g./ml. at 8% moisture) of 1.0.

Other thickeners include carboxymethyl cellulose, hydroxybutyl methyl cellulose, hydroxypropyl methyl cellulose, and preferably hydroxyethyl cellulose (e.g., available as Natrosol).

The poly(methyl vinyl ether/maleic anhydride) thickener is available for example as Gantrez AN 139 (GAF Corporation) and the colloidal silica thickener as a more finely ground Syloid (e.g. 244).

The carboxyvinyl polymer useful as thickener is for example available as Carbopol (e.g. 934, 940, 941). These products of B. F. Goodrich Co. are described in U.S. Pat. Nos. 2,798,053, 2,923,692 and 2,980,655, being essentially colloidally water-soluble acidic carboxylic polymers of acrylic acid crossed-linked with about 0.75 to about 2.0% of a cross-linking agent of polyallyl sucrose or polyallyl pentaerythritol.

The humectant component V, employed in proportions of about 5 to 75, preferably about 10 to 45, more preferably about 15 to 35, wt.% of the toothpaste compositions of this invention is polyethylene glycol (e.g. 400,600). This component of relatively low molecular weight (e.g. about 300 to about 1,000) often also functions as the liquid carrier vehicle, alone or in combination with water and/or ethanol.

Any flavor optionally but preferably employed in the PDP-containing toothpaste compositions of this invention should of course also be compatible with the PDP.

Flavor is typically included in the oral compositions of this invention in approximate weight proportions of 0.01 to 3.0%, preferably 0.5 to 2.0%, more preferably 0.75 to 1.0%. Some illustrative examples of compatible flavors include pulegol, anethole, isoeugenol, guaiacol, creosol, thymol, menthol, cineol, eugenol, clove bud oil, peppermint and spearmint extracts, carvone, methyl paracresol, eucalyptol, safrole, anisol and the like.

The solid and liquid components of the compositions of this invention are proportioned in conventional manner to form a pasty, creamy or gelled mass which may be dispensed or extruded from a pressurized container or from a flexible or collapsible container or tube, e.g. alumina, lined lead or plastic or the like. The compositions may be substantially anhydrous but generally contain about 1 to about 25, typically about 5 to about 20, wt.% of water. These compositions preferably have a pH measured as a 20% aqueous slurry of 7.8 to about 10.5 more preferably about 8.5 to about 10.5, especially about 9.5 to 10.5 since the PDP, especially KPDP, appears to be more stable, i.e. with better retention of active oxygen activity, at these more alkaline ranges in the presence of the other components of the compositions. The pH can be controlled by inclusion of the required amounts of acidic substances such as citric or benzoic acid, basic substances such as sodium hydroxide, and/or buffering agents such as sodium citrate, benzoate, bicarbonate or carbonate, disodium hydrogen phosphate, sodium dihydrogen phosphate, or mixtures thereof. It should be noted that selection of the proper dental abrasive or polishing material is important for maintenance of the above described alkaline pH ranges, since most conventional polishing materials cannot be employed in the instant compositions at such pH ranges. For example, when insoluble sodium metaphosphate (IMP) abrasive is employed with the other above-defined components of these compositions and the pH adjusted to 9.7, the composition loses substantial amounts of its available oxygen when aged at 120° F. and the pH shifts down to about 7.2. In contrast, although compositions of this invention with silica as polishing material show poor stability at an "as is" pH of 7.7 the composition is stabilized when the pH is adjusted upwards as indicated above, e.g. to 9.7, and the pH does not shift significantly with aging. Hydrated alumina performs in excellent manner in this respect since its normal pH falls within the above ranges.

The toothpaste compositions of this invention may contain a non-soap synthetic sufficiently water soluble organic anionic or nonionic surfactant in concentrations generally ranging from about 0.05 to about 10, preferably about 0.5 to about 5, weight percent, to promote wetting, detersive and foaming properties. U.S. Pat. No. 4,041,149 discloses such suitable anionic surfactants in col. 4, lines 31-68 and col. 9, lines 1-12, which passages are incorporated herein by reference thereto. Pluronic type nonionic surfactants (polyoxyethylene polyoxypropylene block polymers) such as Pluronic F108 and F127 may also be employed.

Various other conventional toothpaste adjuvants or excipients may be included such as whitening or coloring agents, preservatives, silicones, ammoniated material such as urea and diammonium phosphate, and sweetening agents in amounts ranging from about 0.01 to about 5 wt.% or more. Suitable sweetening agents include for example sorbitol, xylithol, sodium cyclamate, perillartine, D-tryptophan, dihydrochalcones, and the like, preferably saccharin.

In the practice of this invention, the toothpastes of this invention are applied regularly to the oral cavity, especially dental enamel, preferably from about 1 to 3 times daily, for durations of preferably at least about 10 seconds, more preferably at least about 60 seconds, in the usual required amounts employed in brushing the teeth.

The following examples are further illustrative of the nature of the present invention and are not to be regarded as limitative. All amounts and proportions referred to herein and in the appended claims are by weight unless otherwise indicated.

In the following examples the stability of the KPDP can be evaluated by monitoring active oxygen (A.O.) contents by the following procedure:

KPDP readily hydrolyzes in an acid medium as follows:

$$P_2O_8^{-4} + 2H_2O \rightarrow 2HPO_4^{-2} + H_2O_2$$

An excess of ferrous ammonium sulfate is added to reduce peroxide:

$$2Fe(NH_4)_2(SO_4)_2 + H_2O_2 + H_2SO_4 \rightarrow Fe_2(SO_4)_3 + 2(NH_4)_2SO_4 + 2H_2O$$

The excess of ferrous ion is back titrated with ceric sulfate:

$$2Fe(NH_4)_2(SO_4)_2 + 2Ce(SO_4) \rightarrow Ce_2(SO_4)_3 + Fe_2(SO_4)_3 + 2(NH_4)_2SO_4$$

The A.O. is found by difference.

TABLE I

|  | Example (Wt. %) | | |
| --- | --- | --- | --- |
|  | 1 | 2 | 3 |
| Water, distilled | 19.69 | 17.0 | 18.0 |
| Laponite XLG | 2.4 | 2.4 | 2.5 |
| PEG 600 | 8.7 | 8.0 | 7.0 |
| Pluronic F108 | 4.3 | 4.0 | 4.5 |
| Sodium benzoate | 0.54 | 0.5 | 0.54 |
| Sodium saccharin | 0.22 | 0.2 | 0.22 |
| Flavor | 0.55 | 0.5 | 0.55 |
| Water, distilled | 7.6 | 7.0 | 7.6 |
| KPDP | 3.0 | 3.0 | 3.0 |

TABLE I-continued

| | Example (Wt. %) | | |
|---|---|---|---|
| | 1 | 2 | 3 |
| Hydrated alumina | 53.0 | 50.0 | 53.0 |
| Active Oxygen | | | |
| Theoretical | 0.126 | 0.126 | 0.126 |
| Initial at RT | 0.123 | 0.130 | 0.122 |
| Aged 7 weeks at 100° F. | 0.123 | 0.131 | 0.130 |

TABLE II

| | EXAMPLE (WT. %) | |
|---|---|---|
| | 4 | 5 |
| Laponite XLG | 2.0 | |
| Laponite XLS | | 5.8 |
| Natrosol 250 MR* | 0.5 | |
| KPDP | 3.0 | 3.0 |
| Sodium benzoate | 0.5 | |
| Sodium saccharin | 0.2 | 0.2 |
| PEG 600 | 10.0 | 15.0 |
| Hydrated alumina | 49.0 | 37.0 |
| SLS | 1.5 | 1.5 |
| Flavor | 0.5 | 0.5 |
| Water | 32.8 | 37.0 |
| (pH) | (10.0) | (9.6) |
| ACTIVE OXYGEN | | |
| Initial at RT | 0.124 | 0.127 |
| Aged 3 weeks at 120° F. | 0.130 | 0.127 |
| Aged 6 weeks at 120° F. | 0.120 | 0.112 |
| Aged 9 weeks at 120° F. | 0.116 | 0.119 |

*Hydroxyethyl cellulose

TABLE III

| | EXAMPLE (WT. %) | |
|---|---|---|
| | 6 | 7 |
| Syloid 244 | 7.15 | 7.3 |
| Zeo49 (Huber silica) | 19.36 | 19.8 |
| PEG 600 | 50.6 | 51.7 |
| KPDP | 3.0 | 3.4 |
| Sodium saccharin | 0.2 | 0.22 |
| Sodium benzoate | 0.5 | 0.56 |
| TiO$_2$ | 0.55 | 0.56 |
| Water | 17.14 | 14.8 |
| SLS | 1.0 | 1.66 |
| Flavor | 0.5 | — |
| (pH adjusted with 50% NaOH) | (9.7) | (9.2) |
| ACTIVE OXYGEN | | |
| Initial at RT | 0.125 | 0.148 |
| Aged 3 weeks at 120° F. | 0.118 | 0.126 |
| Aged 6 weeks at 120° F. | 0.110 | 0.128 |
| Aged 9 weeks at 120° F. | 0.108 | 0.132 |

TABLE IV

| | Example (Wt. %) | | |
|---|---|---|---|
| | 8 | 9 | 10 |
| Hydroxyethyl cellulose | 1.0 | 1.0 | 1.0 |
| PEG 600 | 20.0 | 20.0 | 20.0 |
| Sodium benzoate | 0.5 | 0.5 | 0.5 |
| Sodium saccharin | 0.2 | 0.2 | 0.2 |
| Hydrated alumina | 47.0 | 47.0 | 48.0 |
| KPDP | 3.0 | 3.0 | 3.0 |
| H$_2$O | 26.05 | 26.05 | 25.6 |
| Flavor | 0.75 | 0.75 | 0.5 |
| SLS* | 1.5 | 1.5 | — |
| Nonionic Surfactant** | — | — | 1.2 |
| (pH) | (10) | (10) | |
| Active Oxygen | | | |
| Initial at RT | 0.136 | 0.131 | 0.130 |
| Aged 6 weeks at 120° F. | 0.134 | 0.133 | |
| Aged 9 weeks at 120° F. | | | 0.130 |

*Sodium lauryl sulfate
**Polyethoxylated (20 E.O.) sorbitan monoisostearate

The formulations in the above examples exhibit good to excellent active oxygen stability in storage. In contrast, the only toothpaste formulation disclosed in U.S. Pat. No. 4,041,149, namely Example 1, containing incompatible components (glycerine, precipitated calcium carbonate and dicalcium phosphate dihydrate) exhibits unacceptable active oxygen stability. Some of the above examples show the sequence of addition of underlined individual or grouped components.

| | WT. % |
|---|---|
| Natrosol 250 MR | 1.0 |
| PEG 600 | 20.0 |
| Hydrated alumina | 52.0 |
| SLS | 1.5 |
| Sodium benzoate | 0.5 |
| Sodium saccharin | 0.2 |
| KPDP | 3.0 |
| Deionized water | 25.8 |
| (pH at 10.2) | |

The above chemically, physically and cosmetically stable formulation according to this invention and a control formulation omitting the KPDP were evaluated for effectiveness in reducing gingivitis and plaque in a scientifically conducted 12 week test on groups of 10 beagle dogs (5 male and 5 female). The results (average of 10 dogs) were as follows:

| | CONTROL | EXAMPLE 11 |
|---|---|---|
| Gingiva Index | | |
| Initial | 0.85 | 0.88 |
| Final | 0.79 | 0.47 |
| Plaque Unit Index | 1.22 | 0.96 |

These results established that the addition of the KPDP to the control formulation significantly reduced both the gingival index and the plaque index. In contrast, a simultaneous test using a nonaqueous formulation containing propylene glycol humectant, hydroxypropyl cellulose thickener and Dical abrasive increased the plaque index and a similar test using an aqueous neutral formulation containing PEG 600 humectant, hydroxyethyl cellulose thickener and IMP abrasive increased both the gingival and plaque indices.

It has been shown above that formulations according to the invention containing polyethylene glycol (PEG) humectant are highly stable against loss of available oxygen. The criticality of combinations of required components in such formulations, and the mutuality of stabilization therein, is established for example by the fact that PEG acts upon and drastically reduces the effectiveness of KPDP as a source of available oxygen in the absence of the other defined components. Thus, aqueous KPDP solutions buffered to pH 7 are stable at 120° F. for 9 weeks, but the addition of varying amounts (3% 15%, 40%) of PEG to 3% KPDP solutions (conducted in triplicate) yield, when aged 9 weeks at 100° L F. and 120° F., the following average results:

| | % of Available Oxygen | | | | | | |
|---|---|---|---|---|---|---|---|
| | Initial | 1 wk 120° F. | 3 wk 120° F. | 6 wk 120° F. | 9 wks 120° F. | 6 wks 100° F. | 9 wks 100° F. |
| 3% PEG | 0.126 | 0.107 | .050 | 0.041 | 0 | 0.086 | 0.061 |
| 15% PEG | 0.115 | 0.113 | 0.066 | 0.053 | 0.023 | 0.088 | 0.066 |

-continued

| | Initial | 1 wk 120° F. | 3 wk 120° F. | 6 wk 120° F. | 9 wks 120° F. | 6 wks 100° F. | 9 wks 100° F. |
|---|---|---|---|---|---|---|---|
| 40% PEG | 0.120 | 0.116 | 0.091 | 0.084 | 0.029 | 0.091 | 0.072 |
| AVERAGE % LOSS | | 6.7 | 42.4 | 50.4 | 85.2 | 26.5 | 44.9 |

This invention has been disclosed with respect to preferred embodiments, and it will be understood that modifications and variations thereof obvious to those skilled in the art are to be included within the spirit and purview of this application and the scope of the appended claims.

We claim:
1. A toothpaste composition having a pH of about 9.2 to about 10.5 consisting essentially of
   I. an oral vehicle
   II. as essentially the only oral chemically active agents,
      A. 0 to about 2 wt.% of a fluorine-providing anticaries compound and
      B. about 1 to about 7 wt. % of a peroxydiphosphate salt,
   III. as essentially the only polishing material, about 10 to about 75 wt.% of at least one polishing material selected from the group consisting of silica and hydrated alumina,
   IV. about 0.5 to about 10 wt.% of at least one thickener selected from the group consisting of colloidal silica, synthetic hectorite, poly(methyl vinyl ether/maleic anhydride), carboxyvinyl polymer, carboxymethyl cellulose, hydroxypropyl methyl cellulose, hydroxybutyl methyl cellulose, and hydroxyethyl cellulose, and
   V. about 5 to about 75 wt.% of polyethylene glycol as essentially the only humectant.
2. A composition according to claim 1 wherein the polishing material comprises hydrated alumina.
3. A composition according to claim 2 wherein the thickener comprises synthetic hectorite.
4. A composition according to claim 2 wherein the thickener comprises hydroxyethyl cellulose.
5. A composition according to claim 1 wherein the polishing material comprises silica.
6. A composition according to claim 1 wherein said peroxydiphosphate salt is tetrapotassium peroxydiphosphate.
7. A composition according to claim 2 wherein said peroxydiphosphate salt is tetrapotassium peroxydiphosphate.
8. A composition according to claim 4 wherein said peroxydiphosphate salt is tetrapotassium peroxydiphosphate.
9. A composition according to claim 1 having in the form of a 20% aqueous slurry a pH of about 9.5 to 10.5.
10. A composition according to claim 8 having in the form of a 20% aqueous slurry a pH of about 9.5 to 10.5.
11. A method comprising applying to the oral cavity a composition as defined in claim 1.
12. A method comprising applying to the oral cavity a composition as defined in claim 8.
13. A composition according to claim 5 wherein the thickener comprises colloidal silica.
14. A composition according to claim 13 wherein said peroxydiphosphate salt is tetrapotassium peroxydiphosphate.
15. A composition according to claim 3 wherein said peroxydiphosphate salt is tetrapotassium peroxydiphosphate.
16. A composition according to claim 5 wherein said peroxydiphosphate salt is tetrapotassium peroxydiphosphate.
17. A method comprising applying to the oral cavity a composition as defined in claim 6.
18. A method comprising applying to the oral cavity a composition as defined in claim 7.
19. A method comprising applying to the oral cavity a composition as defined in claim 15.
20. A method comprising applying to the oral cavity a composition as defined in claim 16.

* * * * *